United States Patent
Shen et al.

(10) Patent No.: US 11,421,236 B1
(45) Date of Patent: Aug. 23, 2022

(54) BIOSENSOR FOR DETECTING TNT

(71) Applicant: Research Foundation of the City University of New York, New York, NY (US)

(72) Inventors: Chang-Hui Shen, Edison, NJ (US); Robert Corin, Belford, NJ (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 16/851,202

(22) Filed: Apr. 17, 2020

Related U.S. Application Data

(60) Provisional application No. 62/835,209, filed on Apr. 17, 2019.

(51) Int. Cl.
| | |
|---|---|
| *C12N 9/78* | (2006.01) |
| *C12N 9/06* | (2006.01) |
| *C12N 1/20* | (2006.01) |
| *C12N 15/00* | (2006.01) |
| *C07H 21/04* | (2006.01) |
| *C12N 15/62* | (2006.01) |
| *C12N 9/02* | (2006.01) |
| *C12N 15/78* | (2006.01) |
| *G01N 33/543* | (2006.01) |
| *C12Q 1/00* | (2006.01) |

(52) U.S. Cl.
CPC ............ *C12N 15/62* (2013.01); *C12N 9/0044* (2013.01); *C12N 9/0069* (2013.01); *C12N 9/78* (2013.01); *C12N 15/78* (2013.01); *C12Q 1/004* (2013.01); *G01N 33/54373* (2013.01)

(58) Field of Classification Search
CPC ........ C12N 15/62; C12N 9/0044; C12N 9/78; C12N 15/78
See application file for complete search history.

(56) References Cited

PUBLICATIONS

Belkin. Remote detection of buried landmines using a bacterial sensor. Nature Biotechnology. vol. 35 No. 4. Apr. 2017.*

Shemer, B. et al.; Microbial bioreporters of trace explosives; Current Opinion in Biotechnology; Jun. 2017; pp. 113-119; vol. 45; https://doi.org/10.1016/j.copbio.2017.03.003.

Spanggord, R. et al.; Biodegradation of 2,4-Dinitrotoluene by a *Pseudomonas* sp.; Applied and Environmental Microbiology, Nov. 1991; pp. 3200-3205; vol. 57, No. 11.

(Continued)

*Primary Examiner* — Yong D Pak
(74) *Attorney, Agent, or Firm* — Peter J. Mikesell; Schmeiser, Olsen & Watts, LLP

(57) ABSTRACT

A biosensor for detecting nitrotoluenes. Two *P. putida* host populations (H-I and H-II) are engineered. H-1 undergoes fluorescence when a nitrotoluene is detected but it is also engineered to metabolize nitrotoluenes to toluene as its sole nitrogen-source. H-I is 1-ACC Deaminase inactive and is further engineered to efflux toluene and provide toluene to adjacent H-II. In H-II, ACC is the N-source and metabolizes toluene as the sole carbon and energy source available. The H-II cells are engineered to not be able to use medium fructose. The H-II population has a promoter/GFP construct with a promoter sensitive to toluene and thus they fluoresce from that first nitrotoluene metabolite i.e. toluene, produced by the H-I cells. This is achieved by making H-II cells mutants unable to transport and phosphorylate fructose i.e. PTSFRU gene knock-out.

3 Claims, 1 Drawing Sheet

(56) References Cited

PUBLICATIONS

Segura, A. et al.; Proteomic Analysis Reveals the Participation of Energy- and Stress-Related Proteins in the Response of Pseudomonas putida DOT-T1E to Toluene; Journal of Bacteriology; Sep. 2005; pp. 5937-5945; vol. 187, No. 17; doi:10.1128/JB.187.17.5937-5945. 2005.

Lee, A. et al.; Constitutive and Inducible Green Fluorescent Protein Expression in Bartonella henselae; Infection and Immunity; Aug. 1998; pp. 3964-3967; vol. 66, No. 8.

Chen, S. et al.; Simultaneous Analysis of Bacterioferritin Gene Expression and Intracellular Iron Status in Pseudomonas putida KT2440 by Using a Rapid Dual Luciferase Reporter Assay; Applied and Environmental Microbiology; Feb. 2009; pp. 866-868; vol. 75, No. 3; doi:10.1128/AEM.01823-08.

Satrijo, A. et al.; Enhanced Luminescence from Emissive Defects in Aggregated Conjugated Polymers Macromolecules; Nov. 15, 2007; pp. 8833-8841; vol. 40, No. 25; doi:10.1021/ma071659t.

Ahmed, E.; Fluorescent Multiblock π-Conjugated Polymer Nanoparticles for In Vivo Tumor Targeting; Adv Mater.; Aug. 27, 2013; pp. 4504-4510; vol. 25., No. 32; doi:10.1002/adma. 201301656.

\* cited by examiner

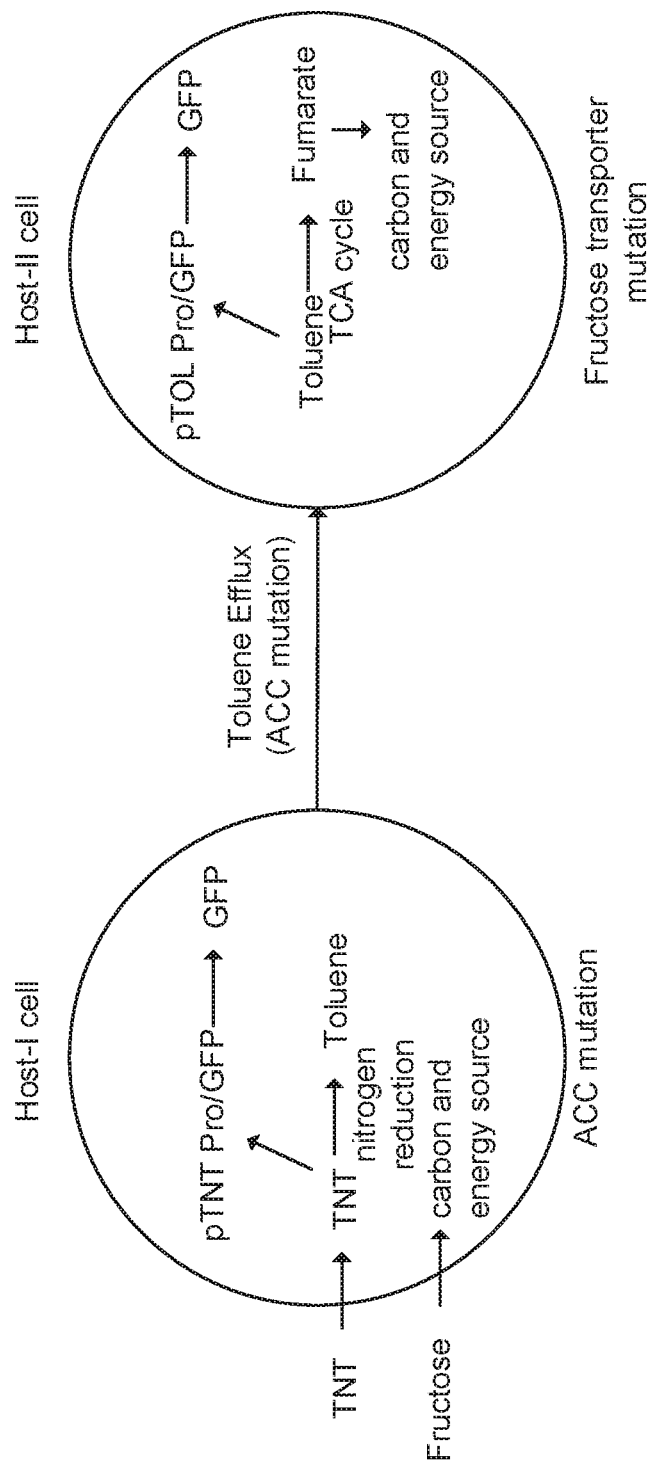

BIOSENSOR FOR DETECTING TNT

CROSS-REFERENCE TO RELATED APPLICATIONS

This application claims priority to and is a non-provisional of U.S. Patent Application 62/835,209 (filed Apr. 17, 2019), the entirety of which is incorporated herein by reference.

BACKGROUND OF THE INVENTION

Two classes of technologies are available for the detection of buried landmines. Onsite detection methods, though very sensitive, are very cumbersome, slow, characterized by a high rate of false positives and—most importantly-require physical presence in the minefield. This poses significant risks to personnel and equipment. Standoff detection methods are being developed for remote detection of explosives and buried landmines. These methods provide fast scan rates of the minefield and do not require immediate access to it, but at present are not sufficiently sensitive to detect the minute traces of explosives that reach the surface of the minefield. Improved detection technology is therefore desired.

The discussion above is merely provided for general background information and is not intended to be used as an aid in determining the scope of the claimed subject matter.

SUMMARY

A biosensor for detecting nitrotoluenes is described. Two *P. putida* host populations (H-I and H-II) are engineered. H-1 undergoes fluorescence when a nitrotoluene is detected but it is also engineered to metabolize nitrotoluenes to toluene as its sole nitrogen-source. H-I is 1-ACC Deaminase inactive and is further engineered to efflux toluene and provide toluene to adjacent H-II. In H-II, ACC is the N-source and metabolizes toluene as the sole carbon and energy source available. The H-II cells are engineered to not be able to use medium fructose. The H-II population has a promoter/GFP construct with a promoter sensitive to toluene and thus they fluoresce from that first nitrotoluene metabolite i.e. toluene, produced by the H-I cells. This is achieved by making H-II cells mutants unable to transport and phosphorylate fructose i.e. PTSFRU gene knock-out.

In a first embodiment, a biosensor for detecting trinitrotoluene is provided. The biosensor comprising: a first *Pseudomonas putida* bacteria host (H-1) that is engineered to employ trinitrotoluene (TNT) as a sole N-source with toluene as a metabolic product, wherein the H-1 has been further engineered to comprise a chimeric DNA molecule with TNT sensitive promoter and fluorescent gene product; and a second *Pseudomonas putida* bacteria (H-2) that is engineered to employ toluene as a sole carbon source, wherein the H-2 has been further engineered to comprise a chimeric DNA molecule with toluene sensitive promoter and fluorescent gene product.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1 is a schematic depiction of a metabolic pathway for engineered strains of *P. putida* Host-I and Host-II cells.

DETAILED DESCRIPTION OF THE INVENTION

This disclosure provides a genetically engineer biosensor that express a dose-dependent amount of fluorescent protein upon sensing the presence of dinitrotoluene (DNT) and trinitrotoluene (TNT). This, in turn, enables the detection of landmines that contain DNT or TNT.

Prior feasibility studies have been published with limited success i.e. proof of concept but are not sensitive enough for use on real minefields. The published system has specificity but still lacks the sensitivity to be useful in searching for existing deployed landmines. This disclosure provides a next generation biosensor that has dramatically increased sensitivity to allow real life detection of landmines. The biosensor detection system for explosive landmines (1) can be delivered on a wide scale to current minefields; (2) has high degree of sensitivity; (3) can be detected easily and rapidly; (4) has a biological sensor that, itself, is safe by making each biological unit self-limiting; (5) cuts the cost to produce biosensors.

In the disclosed system comprises two host bacteria, each with a different promoter/Green Fluorescent Protein (GFP) chimeric constructs. When the first host cell detects a TNT molecule it will fluoresce but it is also engineered to metabolize TNT to toluene and use TNT as its sole nitrogen-source (N-source). Site-directed mutagenesis (gene knock-out) is employed to render 1-aminocyclopropane-1-carboxylic acid (ACC) Deaminase inactive in bacteria *P. putida* (*Pseudomonas putida*) Host-I (H-I). ACC in the medium serves as the N-source for other host cell populations i.e. Host-II. The H-I is further engineered (gene knock-in) to efflux toluene to prevent toluene toxicity (to H-I cells) and provide toluene (carbon & energy source) to adjacent Host-II (H-II) cells. The H-II population has a promoter/GFP construct with a promoter sensitive to toluene and thus they fluoresce from that first TNT metabolite i.e. toluene, produced by the H-I cells. These cells (H-II) are also further engineered (gene knock-in) to metabolize toluene as the sole carbon and energy source available. The H-II cells are a *P. putida* that have a chromosomal toluene catabolic pathway (tod) genes. These cells are engineered to not be able to use medium fructose. This is achieved by making H-II cells mutants unable to transport and phosphorylate fructose i.e. PTSFRU gene knock-out. This scheme is illustrated in Table 1 and FIG. 1. This approach can double fluorescent signal per TNT molecule.

TABLE 1

Summary of engineered strains of *P. putida* Host-I and Host-II cells. pTNT PRO/GFP is Bioreporter-I (B-I); pTOL PRO/GFP is Bioreporter-II (B-II); GFP is green fluorescent protein

|  | Host-I (H-I) | Host-II (H-II) |
| --- | --- | --- |
| Carbon- & Energy Source | fructose | toluene |
| Nitrogen Source | TNT | ACC |
| Gene Knock-out | ACC Deaminase Toluene metabolism | $pTS^{FRU}$ |
| Gene Knock-in | Toluene effluxer |  |
| Plasmid Bioreporter | TNT promoter/GFP pTNT Pro/GFP | Toluene promoter/GFP pTOL Pro/GFP |
| Biochemical reaction | TNT → toluene | toluene → TCA cycle |

Two different host cells (H-I, H-II) are engineered, each to carry a biosensor plasmid with a green fluorescent protein (GFP) gene fused to two different promoters. Unlike previous reports that employed *E. coli*, the disclosed biosensors utilize *P. putida* strains. *P. putida* has been studied extensively and has the advantage of being a normal soil and rhizobial bacteria with no pathogenic potential. In fact, *P. putida* is a root normal flora for crop plants and has been shown to increase crop productivity.

The bacteria used in the biosensor are generated by employing growth based selection (without preceding mutagenesis) to select for cells that display or enhance desired phenotypes. The *P. putida* strains are kept viable and nutritionally responsive to TNT/DNT and their metabolites i.e. toluene, for the duration of the landmine detection period (about 12 hours). Host (H-I & H-II) viability is determined by the efficiency of plating (EOP) during the 12 hour detection phase. The EOP should remain constant during this 12 hours. The biosensor are tested directly by adding TNT or toluene directly to cultures of H-1 and H-II cells and measuring fluorescence. Because *P. putida* is able to catabolize all of the L-amino acids employed for protein synthesis, one can provide a mixture which can be used for the synthesis of GFP. Experience has shown that providing bacteria with such mixtures e.g. from protein digests, may avoid potential toxicity issues with single amino acid additions. *P. putida* was shown to exhibit "crossed catabolite repression" where the organism is able to simultaneously employ two different carbon and energy sources at the same time e.g. glucose and toluene.

Host-1 (H-1): An isolate of *P. putida* has been described that is able to employ TNT as its sole N-source with toluene as a product. This isolated was produced by the in vitro selection for cells with rapid doubling times using TNT as a sole N-source by passing cells continuously in media composed of salts, fructose (0.5% w/v) and TNT as the sole nitrogen-source. Examination of two isolates grown on several N-sources (ammonium, nitrate, or TNT) demonstrated a positive correlation of growth and nitroreductase activity.

In one embodiment a *P. putida* strain is used whose entire genome has been sequenced e.g. *P. putida* KT2440. Cells are cultured at 30° C. in M9 minimal medium as described with fructose (0.5% w/v) as the carbon-source and TNT as the nitrogen-source. Because TNT is quite toxic, one can stepwise select for cells that grow and use TNT as a nitrogen-source. Cells are grown in liquid culture and TNT toxicity can be estimated by growth yield employing light scattering (Absorbance at 600 nm, A600 nm) v TNT concentration from 1 to 100 mg/L (limit of solubility). Based upon these results, the effective concentration for 50% inhibition of growth ($EC_{50}$) is estimated. The $EC_{50}$ for TNT is the starting concentration to grow cells. Growth is monitored by $A_{600nm}$. When growth rate and yield increase and are similar to growth in M9 medium without TNT but a comparable amount of nitrogen from nitrate, the concentration of TNT is doubled in the selection. This procedure is repeated until rapid growth to high yields with TNT (0.1-1.0 grams/L) is achieved as the sole nitrogen-source for cells. In parallel with the stepwise increase in TNT concentration, the medium may be analyzed for products of TNT metabolism by NMR spectroscopy. Cells with the greatest yield of toluene made from TNT are of interest. Cells can be cloned on agar M9 plates made with TNT (100 mg/L). A number of clones can be isolated, tested for toluene production, and stored on agar plates at 4° C. The cells that grow well in high TNT concentrations and convert TNT to toluene efficiently are the starting population to make the H-I cell.

The following modifications are made to the selected clone. Genomic alterations include the site directed mutagenesis (knock-outs) of the gene for 1-aminocyclopropane-1-carboxylic acid (ACC) deaminase. This is because ACC is included in the medium for the final biosensor as a nitrogen-source for the H-II cells. The H-1 cell is be made unable to metabolize toluene (FIG. 1). Either chromosomal or plasmid derived, the H-I cells will be knockouts for both the upper and lower pathways of toluene metabolism.

The CRISPER technology may be utilized to add more functional genes to the H-I chromosome i.e. the genes for toluene efflux and nitroreductase genes. The PnrA, PnrB, and PnrC genes codes for nitroreductase. It is reasoned that adding more nitroreductase (even if already present) will increase the efficiency of TNT→toluene conversion. The toluene efflux protein is responsible for the tolerance of Pseudomonads to toluene toxicity. The Ramos lab (J of Bacteriology, September 2005, p5937-5945) has described constitutively expressed toluene efflux genes (ttgABC genes) that make *P. putida* tolerant to toluene as well as other solvents. It is also reasoned that the presence of additional toluene efflux activity in H-I will increase the productivity of H-II.

Host-II (H-II): For the H-II population, *P. putida* DOT-T1E strain is used since it has chromosomal genes i.e. the tod genes that allow use of toluene through the citric acid (TCA) cycle as a source of carbon and energy. The medium contains ACC as a nitrogen-source. These cells are unable to employ the fructose in the medium after H-II cells have directed mutation of the fruB gene responsible for transport and phosphorylation of fructose. This H-II population is engineered to be unable to metabolize TNT i.e. knock-out all functional genes for nitro reductase PnrA, PnrB, and PnrC. This makes more DNT/TNT available to H-I cells that have a TNT/DNT responsive biosensor. Toluene will be metabolized through the TCA cycle.

Biosensor-I (B-I): The biosensor B-I is expressed in the engineered *P. putida* host bacteria H-1. The biosensor itself is a TNT/DNT responsive element made according to the Belkin group (Belkin, B., Yagur-Kroll, S., Kabessa, Y., Korouma, Y., Septon, T., Yonatan Anati, Cheinat Zohar-Perez, Zahi Rabinovitz, Amos Nussinovitch, A., Agranat, A. J. 2017. Remote detection of buried landmines using a bacterial sensor. Nature Biotechnology. 35: 308-310). A directed evolution was employed to increase the yqiF promoter performance in detection of TNT/DNT.

A FACS-optimized GFP gene may be obtained, for example, as described by the Falkow laboratory (Infection and Immunity, August 1998, p. 3964-3967) identified as $GFP_{mut}$. This same $GFP_{mut}$ gene is employed in the construction of the other biosensor (B-II, below).

Biosensor-II (B-II): The biosensor B-II in the engineered *P. putida* bacteria H-II is a construct of the toluene sensitive promoter found in the TOL plasmid pWWO fused with the GFP. A similar biosensor expressed in *P. putida* has been described the only difference being that biosensor construct pGLTUR employed a luciferase reporter. In the disclosed biosensor this is replaced with a GFP gene. This system was highly sensitive to toluene and when compared to standard gas chromatography-mass spectroscopy gave identical results for toluene contamination of well water i.e. 5.7 and 7.4 ppm in two separate trials.

Encapsulation materials: The disclosed solution to the sensitivity problem also has a chemically engineered component. Instead of using agar for encapsulation (and delivery) of the biosensor as previous described, some embodiments employ micro- or nanosilicate particles. It has been elegantly demonstrated by the Swager group at M.I.T. (Macromolecues, 2007, 40(25) p. 8833-8841; Adv. Materi. 2013 Aug. 27, 25(32), p. 4504-4510) that conjugated polymers (CP) can greatly amplify fluorescent signals. Additionally, studies have already demonstrated that the CP can be deposited on micro- and nanoparticles of silicate and retain the ability to amplify fluorescent signal. Methods exist to mix CP-coated silicate particles with cells and make thin films of these mixtures by centrifugation onto a slide. This method (layer by layer, LbL) allows the creation of layers with differing compositions. A macroscopic 3-dimensional particle aspect may be utilized in construction of the final biosensor. The cells are packed tightly enough (e.g. within 10 microns) to optimize availability of toluene to go from H-I→H-II cells e.g. possibly with overlapping unstirred layers. In one embodiment a microbial assembly line is used with each stop producing GFP and an encapsulation (delivery system for biosensors) that is proven to dramatically increase fluorescent signals. Therefore, the disclosed system is extremely sensitive and cost-effective.

There are two components to the disclosed encapsulation procedure that are helpful in making a sensitive and useful landmine detector. First silicates, rather than agar, is employed as previously described. It has been demonstrated that silicates can increase fluorescent signals up to 1.8-fold over an agarose encapsulation. Far more important is that the Swager group at MIT has already demonstrated in numerous publications that conjugated polymers can tremendously enhance fluorescent signals. Furthermore, the fluorescent properties of conjugated polymers are retained when silicate microspheres and nanospheres are coated with conjugated polymers. These particles are built up with a layer by layer (LbL) approach where a thin film of particles are centrifuged onto a glass slide i.e. that constitutes one layer. Further layers are deposited by repeating the centrifugation step. Finally, conjugated polymers are made from water soluble monomers.

The biosensor of silicate CP-coated microparticles mixed with the desired bacterial populations enables one to optimize the signal response to landmines by maximizing the likelihood that the TNT/DNT sensitive cells will be the cells that are in contact with the environment (i.e. the soil above landmines that is the source of TNT/DNT). This is achieved by constructing biosensor particles that have an outer layer composed of H-I cells bearing the plasmid (B-I) in the outer layer. The inner aspect of the particles are composed of the silicate CP-coated microparticles mixed with H-II cells bearing plasmids B-II.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A biosensor for detecting trinitrotoluene, the biosensor comprising:
   a first *Pseudomonas putida* bacteria host (H-1) that is engineered to employ trinitrotoluene (TNT) as a sole N-source with toluene as a metabolic product, wherein the H-1 has been further engineered to comprise an inactivated endogenous 1-aminocyclopropane-1-carboxylic acid (ACC) deaminase, an *Escherichia coli* yqiF TNT-sensitive promoter linked to a green fluorescent protein (GFP), a chimeric DNA molecule with TNT sensitive promoter and fluorescent gene product; and
   a second *Pseudomonas putida* bacteria (H-2) that is engineered to employ toluene as a sole carbon source, wherein the H-2 has been further engineered to comprise an inactivated endogenous nitro reductase PnrA, PnrB and PnrC, a toluene-sensitive promoter from a TOL plasmid pWWO from *Pseudomonas putida* that is linked to a green fluorescent protein (GFP), a chimeric DNA molecule with toluene sensitive promoter and fluorescent gene product.

2. The biosensor as recited in claim 1, wherein the H-1 is 1-aminocyclopropane-1-carboxylic acid (ACC) deaminase inactive, metabolizes dinitrotoluene and trinitrotoluene to toluene as the sole nitrogen source, and comprises a trinitrotoluene promoter and green fluorescent protein (GFP) gene.

3. The biosensor as recited in claim 2, wherein the H-2 is 1-aminocyclopropane-1-carboxylic acid (ACC) deaminase active, is unable to metabolize fructose but metabolizes toluene, and comprises a toluene promoter and green fluorescent protein (GFP) gene.

* * * * *